(12) United States Patent
Martinez

(10) Patent No.: US 7,536,736 B1
(45) Date of Patent: May 26, 2009

(54) CHILD'S NECK PILLOW

(76) Inventor: Rachel A. Martinez, 873 SW. 149 Ct., Miami, FL (US) 33194

( * ) Notice: Subject to any disclaimer, the term of this patent is extended or adjusted under 35 U.S.C. 154(b) by 0 days.

(21) Appl. No.: 12/292,140

(22) Filed: Nov. 12, 2008

(51) Int. Cl.
*A47G 9/00* (2006.01)
(52) U.S. Cl. .................. 5/639; 5/421; 5/490; 5/640
(58) Field of Classification Search .............. 5/639, 5/490, 655, 421, 636, 640; D6/601
See application file for complete search history.

(56) References Cited

U.S. PATENT DOCUMENTS

| | | | | |
|---|---|---|---|---|
| 2,961,668 A | * | 11/1960 | Hayes | 5/640 |
| 4,197,604 A | * | 4/1980 | Nakamura | 5/640 |
| 4,776,049 A | | 10/1988 | Perron | |
| 4,783,866 A | * | 11/1988 | Simmons et al. | 5/639 |
| 5,027,457 A | * | 7/1991 | Sweet | 5/640 |
| 5,168,590 A | * | 12/1992 | O'Sullivan | 5/490 |
| D370,585 S | * | 6/1996 | Faithfull | D6/599 |
| D430,442 S | | 9/2000 | Reithmeier | |
| 6,216,298 B1 | | 4/2001 | Oliveira | |
| D469,541 S | | 1/2003 | Cheatham | |
| 2004/0200004 A1 | | 10/2004 | Matthews Brown et al. | |

* cited by examiner

*Primary Examiner*—Alexander Grosz
(74) *Attorney, Agent, or Firm*—Richard C. Litman

(57) ABSTRACT

The child's neck pillow is a device that can be employed to provide comfort and support for a child when the child is riding in a vehicle. The pillow is designed to fit around the child's neck and includes legs that fall forward over the child's body. The legs may have mating fasteners to secure the legs together to prevent the child's head from falling forward. A sleeve is provided to encase the pillow. The sleeve can be removed for washing. The sleeve may hold ice or medicinal packs.

8 Claims, 3 Drawing Sheets

CHILD'S NECK PILLOW

BACKGROUND OF THE INVENTION

1. Field of the Invention

The present invention generally relates to safety devices, cushions and pillows, and more particularly to a child's neck pillow used to support the head of a child when the child is seated in a vehicle.

2. Description of the Related Art

There have been many attempts to provide a child (both infants and older children) with proper head and neck support when the child is seated in a vehicle (car, airplane, bus, etc.). Whether asleep or awake, the child should be provided with an effective support keep the head from falling forward to ensure comfort and to prevent or minimize injury. Unfortunately, it is sometimes necessary to transport a child when the child is feverish or overheated. It would certainly be advantageous if a cooling system were incorporated in a head support device for the child to also alleviate this situation. Thus, a child's neck pillow solving the aforementioned problems is desired.

SUMMARY OF THE INVENTION

The child's neck pillow is a device that can be employed to provide comfort and support for a child when the child is riding in a vehicle. The pillow is designed to fit around the child's neck and includes legs that fall forward over the child's body. The legs may be fastened together with mating fasteners to prevent the child's head from falling forward. Fabricated in various colors and animal shapes (frogs, tigers, ducks, etc.), the pillow is designed to be visually attractive to children. A sleeve is provided to encase the pillow. The sleeve can be removed for washing. In one embodiment, the sleeve holds ice or a medicinal pack.

Accordingly, the invention presents a pillow for supporting a child's head, which pillow is effective and fun to use. The pillow can be provided with cooling and/or therapeutic packs. The invention provides for improved elements thereof in an arrangement for the purposes described that are inexpensive, dependable and fully effective in accomplishing their intended purposes.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
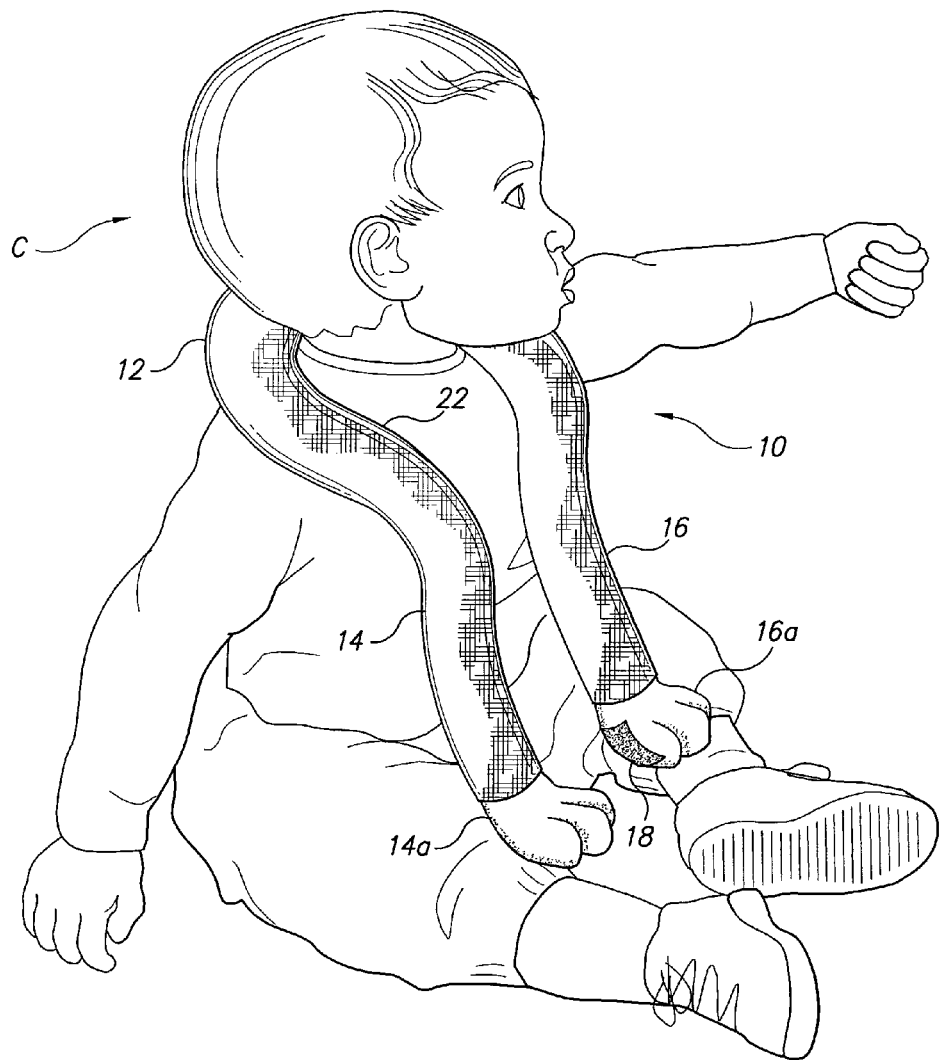
FIG. 1 is an environmental, perspective view of a child's neck pillow according to the present invention.
Figure 2:
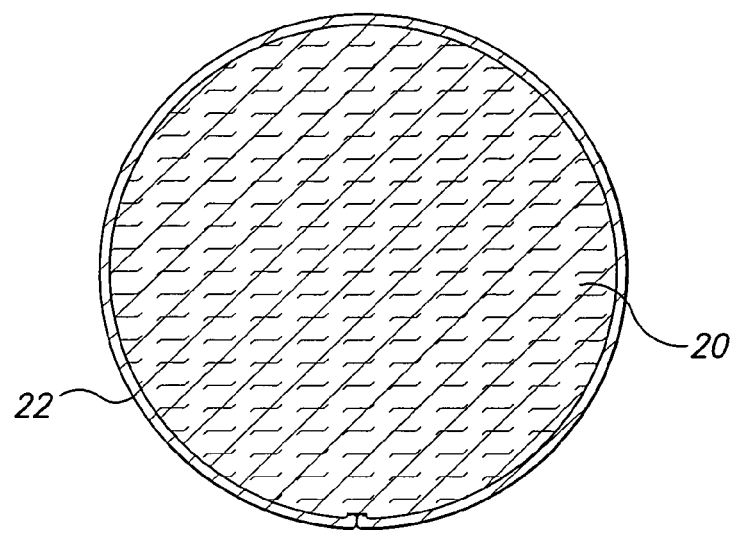
FIG. 2 is transverse section view of a child's neck pillow according to the present invention.

Attention is first directed to FIGS. 1 and 2, wherein the pillow of the instant invention is generally indicated at 10. Pillow 10 is substantially U-shaped and includes a head support portion 12 that is adapted to be positioned at the back of the neck of a seated child C. Legs 14, 16 extend from respective sides of support portion 12 and terminate in respective free ends 14a, 16a. Hook and loop fasteners 18 are disposed on each free end so that the ends 14a, 16a may be fastened together across the child's body. As noted above, support portion 12 and legs 14, 16 are fabricated in various colors and animal shapes to be visually attractive to children. Ends 14a, 16a can be designed replicate animal feet or the like.

A sleeve or sock 22 is utilized to cover the pillow 10. The sleeve 22 encases neck portion 12 and legs 14, 16, leaving the free ends 14a, 16a exposed. Sleeve 22 is easily removed from the pillow for washing. The pillow is fabricated from a suitable polyfiber fill 20, and the sleeve 22 is fabricated from any suitable soft, washable fabric. There is enough polyfiber fill to make the pillow soft, but that still manages to prevent the child's head from falling forward. Additional or replacement sleeves 22 may be provided to replace the sleeve 22 when it is removed for washing.

Figure 3:
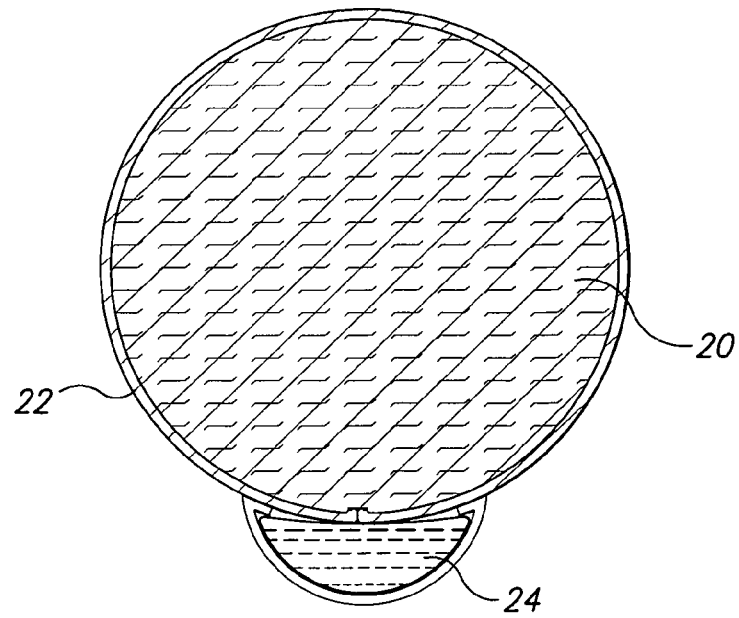
FIG. 3 is a transverse section view of an embodiment of a child's neck pillow according to the present invention having an ice or medicinal pack permanently disposed in the sleeve.
Figure 4:
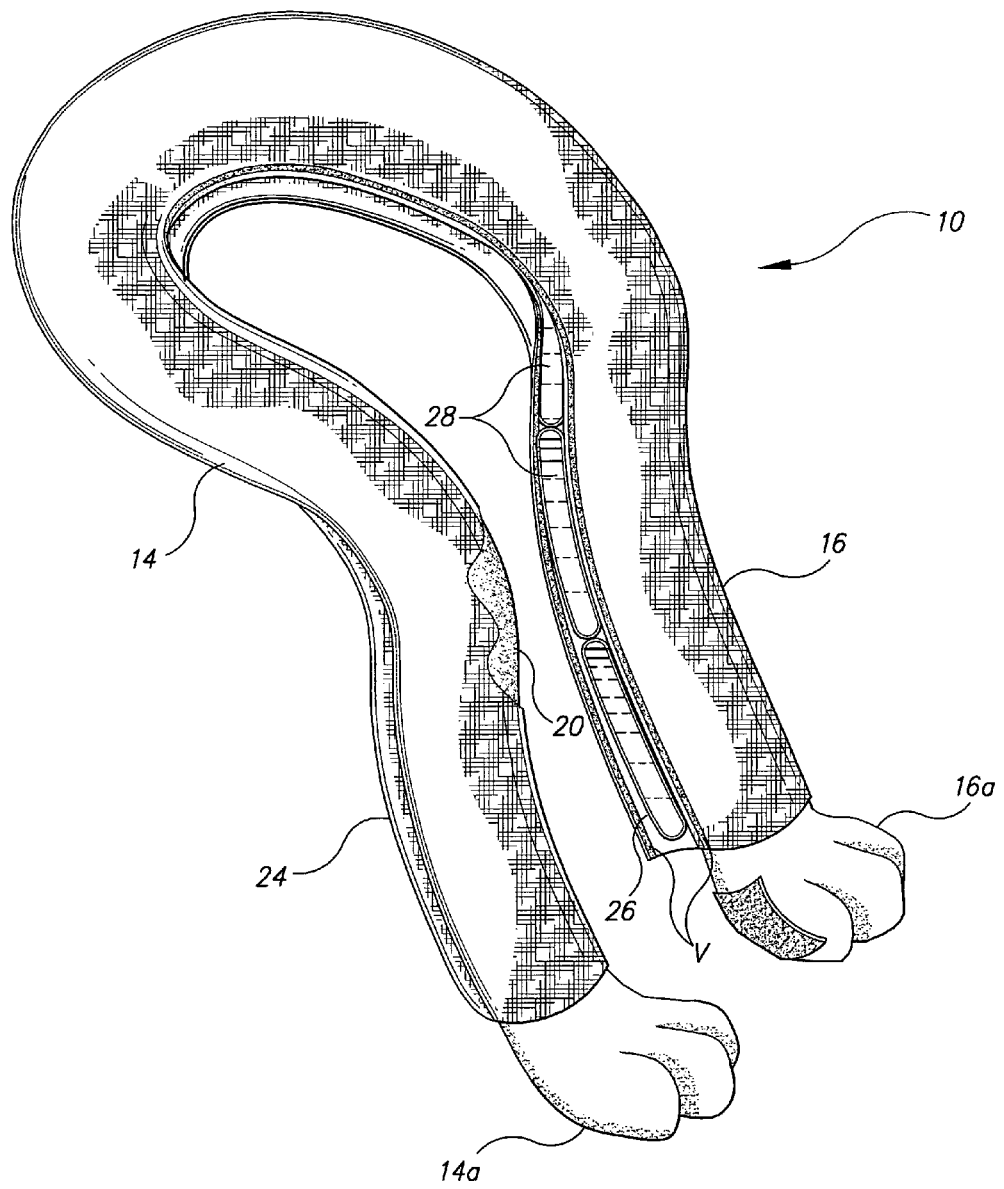
FIG. 4 is a perspective view of an embodiment of a child's neck pillow according to the present invention having an ice or medicinal pack removably disposed in the sleeve.

As best illustrated in FIG. 3, sleeve 22 may include a permanently built-in icepack 24 to provide a cooling medium, if needed, for a feverish child. It should be noted that sleeves 22 may also be provided without an icepack for normal use. Alternatively, FIG. 4 discloses a sleeve having a compartment for removably inserting packs 28 therein via a closable opening 26. Hook and loop fasteners V or any other releasable fastener, e.g., a zipper, may be used to retain the packs 28 in the compartment. Packs 28 can take the forms of icepacks, or they may contain a medicinal agent, such as menthol.

It is to be understood that the present invention is not limited to the embodiments described above, but encompasses any and all embodiments within the scope of the following claims.

I claim:

1. A substantially U-shaped neck support pillow, comprising:
   a padded cushion having a neck support portion;
   a pair of leg portions connected with and extending from the neck support portion, each of the respective leg portions terminating in a distinctive free end, the cushion and the leg portions forming a substantially U-shaped pillow;
   a sleeve having two end portions removably disposed on the padded cushion, the sleeve encasing the neck support portion and the pair of leg portions, the free ends being exposed;
   an elongated compartment incorporated in the sleeve, the compartment being disposed in the sleeve between its end portions, the compartment having a reclosable opening;
   multiple therapeutic packs housed in the compartment.

2. The substantially U-shaped neck support pillow according to claim 1, wherein said padded cushion is fabricated from a polyfiber fill material.

3. The substantially U-shaped neck support pillow according to claim 1, wherein said sleeve is fabricated from a soft, washable fabric.

4. The substantially U-shaped neck support pillow according to claim 1, wherein said multiple therapeutic packs are ice packs.

5. The substantially U-shaped neck support pillow according to claim 1, wherein said multiple therapeutic packs are medicinal packs.

6. The substantially U-shaped neck support pillow according to claim 1, further comprising mating hook and loop fasteners disposed on each of the free ends.

7. The substantially U-shaped neck support pillow according to claim 1, wherein said multiple therapeutic packs are removably housed in said compartment.

8. The substantially U-shaped neck support pillow according to claim 1, wherein said multiple therapeutic packs are permanently incorporated in said sleeve.

* * * * *